United States Patent
Yamaoka et al.

(10) Patent No.: US 8,834,887 B2
(45) Date of Patent: Sep. 16, 2014

(54) DRUG FOR SUPPRESSING PATHOGEN OCCURRING IN VIVO

(75) Inventors: Tetsuji Yamaoka, Suita (JP); Mariko Shiba, Suita (JP); Atsushi Mahara, Suita (JP); Yoshihito Kato, Tokyo (JP)

(73) Assignees: National Cerebral and Cardiovascular Center, Suita (JP); Kowa Co., Ltd., Nagoya-shi (JP)

( * ) Notice: Subject to any disclaimer, the term of this patent is extended or adjusted under 35 U.S.C. 154(b) by 153 days.

(21) Appl. No.: 12/679,395

(22) PCT Filed: Sep. 25, 2008

(86) PCT No.: PCT/JP2008/002652
§ 371 (c)(1),
(2), (4) Date: Mar. 22, 2010

(87) PCT Pub. No.: WO2009/041037
PCT Pub. Date: Apr. 2, 2009

(65) Prior Publication Data
US 2010/0209441 A1    Aug. 19, 2010

(30) Foreign Application Priority Data
Sep. 26, 2007    (JP) ................ 2007-249275

(51) Int. Cl.
*A61K 39/00*     (2006.01)
*A61K 39/385*    (2006.01)
*A61K 47/48*     (2006.01)
*A61K 38/16*     (2006.01)
*C07K 16/28*     (2006.01)
*A61K 31/737*    (2006.01)

(52) U.S. Cl.
CPC ....... *A61K 47/4823* (2013.01); *A61K 2039/505* (2013.01); *A61K 47/48092* (2013.01); *A61K 38/164* (2013.01); *C07K 16/2833* (2013.01); *A61K 31/737* (2013.01)
USPC .................. 424/184.1; 424/193.1; 424/194.1

(58) Field of Classification Search
None
See application file for complete search history.

(56) References Cited

U.S. PATENT DOCUMENTS

| | | | |
|---|---|---|---|
| 4,859,449 A | | 8/1989 | Mattes |
| 5,011,930 A | | 4/1991 | Fujikawa et al. |
| 5,102,888 A | | 4/1992 | Fujikawa et al. |
| 5,229,490 A | * | 7/1993 | Tam .................... 530/324 |
| 5,418,061 A | | 5/1995 | Parham et al. |
| 5,762,930 A | * | 6/1998 | Fanger et al. ........... 424/136.1 |
| 5,783,400 A | * | 7/1998 | Gebski et al. ............ 435/7.4 |
| 5,817,789 A | | 10/1998 | Heartlein et al. |
| 6,027,921 A | | 2/2000 | Heartlein et al. |
| 6,858,578 B2 | | 2/2005 | Heartlein et al. |
| 6,878,269 B2 | | 4/2005 | Nanko et al. |
| 7,022,322 B2 | | 4/2006 | Koll et al. |
| 7,279,106 B2 | | 10/2007 | Nanko et al. |
| 2003/0027233 A1 | * | 2/2003 | Collins et al. ........... 435/7.92 |
| 2008/0107622 A1 | * | 5/2008 | Platt et al. .............. 424/85.2 |
| 2008/0241268 A1 | * | 10/2008 | Gaiger et al. ............ 424/499 |
| 2010/0297187 A1 | * | 11/2010 | Stoloff et al. ........... 424/272.1 |

FOREIGN PATENT DOCUMENTS

| | | |
|---|---|---|
| JP | 1 221400 | 9/1989 |
| JP | 1 279856 | 11/1989 |
| JP | 6 269500 | 9/1994 |
| JP | 8-253430 | 10/1996 |
| JP | 9 266948 | 10/1997 |
| JP | 11 507046 | 6/1999 |
| JP | 11 509084 | 8/1999 |
| JP | 2002 504831 | 2/2002 |

OTHER PUBLICATIONS

Ballerstadt et al (Analytica Chimica Acta vol. 345, pp. 203-212, 1997).*
Ong et al (Cancer Research vol. 51, pp. 1619-1626, 1991).*
Yin et al (J. Biomed. Mater Res. vol. 67, pp. 1093-1104, 2003).*
"Guidelines for management of patients with chronic heart failure in Australia", MJA, vol. 174, pp. 459-466, May 7, 2001.
Japanese Office Action issued May 21, 2013, in Japan Patent Application No. 2009-534176 (with English translation).

* cited by examiner

*Primary Examiner* — Albert Navarro
(74) *Attorney, Agent, or Firm* — Oblon, Spivak, McClelland, Maier & Neustadt, L.L.P.

(57) ABSTRACT

To provide a drug for actively metabolizing or excreting a pathogen occurring in vivo.
The present invention is directed to a compound which is formed of (A) an adsorbent for a pathogen occurring in the blood or lymph, and (B) a ligand which is specific to an organ or cells capable of metabolizing or excreting the pathogen and which is bonded to the adsorbent via a linker or with no linker, and to a drug containing the same.

8 Claims, 5 Drawing Sheets

Incorporation of fluorescent-labeled antibody into HepG2 cells (pre-incubation of HepG2 cells in LDL-free medium for 3 hours (black) and 24 hours (white)

(A) Addition of LDL, F-AB, and DexS-PA to medium (B) Addition of LDL and F-AB to medium (C) Addition of F-AB and DexS-PA to medium

# DRUG FOR SUPPRESSING PATHOGEN OCCURRING IN VIVO

CROSS-REFERENCE TO RELATED APPLICATIONS

This application is a National Stage of PCT/JP08/002652 filed Sep. 25, 2008 and claims the benefit of JP 2007-249275 filed Sep. 26, 2007.

TECHNICAL FIELD

The present invention relates to a drug for actively metabolizing or excreting a pathogen occurring in vivo.

BACKGROUND ART

There are a large number of diseases which are caused by disordered metabolism of lipid, sugar, protein, or endocrine substances. In healthy people, the levels of these substances in the body are generally maintained at constant levels, and excessive amounts of these substances are actively excreted via specific metabolism routes. However, if a specific metabolism route is disordered for a certain reason, a substance to be metabolized is circulated and accumulated in the body, causing an increase in the level of the substance and a variety of diseases. One example of such diseases is hyperlipidemia, which involves an abnormal increase in level of serum lipid (mainly cholesterol, triglyceride, phospholipid, and free fatty acids). Hyperlipidemia is categorized according to the standards. When the fasting serum LDL cholesterol level is 140 mg/dL or higher, this condition is defined as hyper-LDL-cholesterolemia, and when the fasting triglyceride level is 150 mg/dL or higher, this condition is defined as hyper-triglyceridemia. Particularly, hyper-LDL-cholesterolemia is thought to be a main cause for coronary diseases and cerebrovascular disorders, and occurrence of these diseases is reduced by controlling the blood LDL cholesterol level, supported by sufficient evidence.

The treatment of hyperlipidemia employs various drugs such as statin drugs, fibrate drugs, nicotinic acid, anion-exchange resin, cholesterol absorption inhibitors, probucol, dextran sulfate, and ethyl icosapentate. Recently, statin drugs such as pravastatin, sinvastatin, fluvastatin, atorvastatin, pitavastatin, and rosuvastatin are mainly employed in the treatment. Among statin drugs, pitavastatin or a salt thereof is known to exhibit intense HMG-CoA reductase inhibitory effect and serve as a useful blood cholesterol level lowering agent (Patent Document 1). According to the Japan Arteriosclerosis Society Guidelines, the target LDL cholesterol level of a patient is determined in accordance with the number of risk factors for arteriosclerosis of the patient. When a statin is employed in a high-risk group, only about 25% of the patients can clear the target level. Homo-type familial hypercholesterolemia is a type of hereditary disease involving defect of an LDL receptor gene. Since a statin drug works by the action mechanism of activating the LDL receptor, the treatment by statin is no longer effective for a patient of this type. Generally, blood LDL (low-density lipoprotein) is incorporated into the liver by the mediation of the LDL receptor which is present on the surface of liver parenchyama cells, and an excessive amount of LDL is excreted as bile. The patients of homo-type familial hypercholesterolemia have a defect in this function. In addition, the serum cholesterol level is as high as 600 to 1,000 mg/dL, and arteriosclerosis progresses from early childhood, resulting in juvenile heart infarction.

For the treatment of this disease, there have been carried out clinical trials of the gene therapy in which the deficient LDL receptor gene is incorporated. However, the safety of such gene therapy has not yet been established, and many problems to be solved remain for practical employment of the gene therapy. Another possible alternative therapy is liver transplantation. However, since the liver function itself of the patient is normal, liver transplantation is ethically problematic and not realistic therapy. Thus, such severe hypercholesterolemia patients are treated through LDL apheresis, which is a technique in which blood is caused to flow through a column which specifically adsorbs LDL (dextran sulfate cellulose column), to thereby selectively adsorb LDL for removal. The technique can be performed for a long period of time with high safety. However, since LDL apheresis is a plasma exchange technique based on extracorporal circulation, a patient of an age under 5 or 6 cannot receive the therapy. Therefore, arteriosclerosis progressing from the birth of the patient cannot be treated. In addition, cost of the therapy is very high, and the physical load of the therapy is heavy to the patient. Thus, from the viewpoint of enhancement of QOL of the patient, it is desired to establish a new therapy.

For certain reasons, in the patients which undergo blood dialysis, there are observed, in the body, disordered metabolism of water and electrolytes, accumulation of various nitrogen metabolites, and kidney-related hormone abnormality. Generally, substances toxic to the body are excreted through the kidneys, the liver, the gastrointestinal tract, etc. In renal failure patients, excretion of toxic substances through the kidneys requires a longer time, which aggravates renal function disorders and adversely affects other organs. In some cases, the renal failure is fatal.

In the above case, continuous ambulatory peritoneal dialysis and blood dialysis are most generally employed as alternative treatments. According to the statistics of Japan Society for Dialysis Therapy (as of the end of December, 2004), chronic patients requiring dialysis numbers 248,166, and the number of survivals over 20 years is 15,899 (6.7%), with the longest dialysis history of the patients being 37 years and 3 months.

As the period of dialysis becomes longer, dialysis amyloidosis is actually observed as a complication. In renal failure patients, excretion of β2 microglobulin (middle-size protein) is impeded by failure and disorders of renal functions, resulting in high blood β2 microglobulin level. Accumulation of β2 microglobulin causes dialysis amyloidosis. As a result, amyloid fiber deposits in the entire body of an dialysis amyloidosis patient, leading to disorders of bones, nerves, and joints, involving pain and numbness. In this case, QOL of the patient is considerably deteriorated.

In the treatment of dialysis amyloidosis, β2 microglobulin, which is a causal substance, is removed. From the early stage, there have been employed a dialysis technique of high β2 microglobulin removal performance, hemodialysisfiltration (HDF), and a dialyzer having a dialysis membrane having a large pore size (high-performance membrane). Online HDF has gradually come to be employed, in which plasma is actively extracted from blood, and an almost equivolume of liquid replacement is perfused, thereby purifying dialysis liquid during perfusion. If the condition of the patient is grave, surgical treatment is carried out. Cost of these therapies is very high, and the physical load of such a therapy is heavy to the patient. Thus, from the viewpoint of enhancement of QOL of the patient, it is desired to establish a new therapy.

Meanwhile, an auxiliary tool for enhancing the therapeutic effect of a medical column for extracorporeal circulation is also employed. Specifically, hexadecyl-group-immobilized cellulose beads (Lixelle, registered trademark), which specifically bind to β2 microglobulin, is employed (Patent Document 2). It has also been reported that joint pain and the like of dialysis amyloidosis patients are mitigated through hemoadsorption employing hexadecyl-group-immobilized cellulose beads. However, these auxiliary tools for enhancing the therapeutic effect of a medical column for extracorporeal circulation must be used in combination with an anti-clotting agent, or the medical column for extracorporeal circulation must be imparted with an antithrombotic property. Use of an anti-clotting agent imposes a load to the patients, and some patients exhibit shock conditions upon use of heparin, which is a widely employed anti-clotting agent. Therefore, it is desired to establish a new therapy.

In the therapy of a severe hyperlipidemia patient, the therapy of removing an excessive amount of a substance occurring in the body due to certain metabolic disorders, excretion failure, difficulty in removal, etc. (e.g., removal of LDL and removal of β2 microglobulin from dialysis amyloidosis patients), hemodialysis and various apheresis techniques are generally carried out. However, as described above, these methods involve problems of QOL of the patients and high medical cost. Therefore, there is keen demand for new therapeutic means replacing hemodialysis and various apheresis therapeutic techniques.

Idiopathic dilated cardiomyopathy (DCM) is a chronic and progressive disease which involves considerable dilation of the heart lumen, resulting in myocardial contraction failure and which has bad prognosis with a clinical picture showing congestive heart failure. According to an investigation carried out in 1999 by the Ministry of Health and Welfare, the number of patients in Japan was estimated to 17,700. However, since there are many subclinical patients, the actual number is thought to be greater than 17,700.

At present, one radical therapeutic method for DCM is typically heart transplantation in which the heart is transplanted from a brain-death donor. In Japan, the concept "brain death" is not widely accepted by people, and heart transplantation is not often performed. Throughout the world, the number of heart donors is smaller than the patients requiring heart transplantation, which is problematic. Since heart transplantation is not supported by the medical security system, the patient who undergoes transplantation is charged a high medical fee, even when a heart donor has been found. Furthermore, if transplantation is successfully complete, the patient must take an immuno-suppressor for the rest of his or her life. Therefore, the patient is susceptible to suffer an infection disease due to the suppressed immune system, which is a severe problem. Thus, as medical therapy, an angiotensin-converting enzyme inhibitor and a β-blocker are administered in combination to the target patients, and good therapeutic results are obtained (Non-Patent Document 1). However, in some cases the expected effect fails to be attained, depending on the body constitution and progress of the disease condition. In addition, since the medical therapy can only retard the progress of the disease, there is keen demand for therapeutic means for radically treating DCM based on medical therapy.

Patent Document 1: JP-A-1989-279866
Patent Document 2: JP-A-1997-266948
Non-Patent Document 1: Med. J. Aust., 2001, 174, 459-466

DISCLOSURE OF THE INVENTION

Problems to be Solved by the Invention

An object of the present invention is to provide a drug for actively lowering the intracorporal level of a pathogen occurring in vivo.

Means for Solving the Problems

In view of the foregoing, the present inventors have conducted extensive studies, and thought that if there can be provided a drug for actively introducing a pathogen occurring in vivo from the intrinsic metabolism route to another route, the drug would serve as a drug for lowering the intracorporeal level of such a pathogen occurring in vivo based on a new mechanism (called a "metabolic switching mechanism"). Thus, the present inventors have found that a compound which is formed by modifying dextran sulfate serving as an LDL adsorbent with galactose serving as a hepatocyte asialoorosomucoid receptor ligand can transfer LDL into the blood to hepatocytes, to thereby decompose the LDL in the liver, whereby the blood LDL level is significantly lowered.

The present inventors have also found that an LDL-dextran sulfate-β2 microglobulin antibody complex, which is formed during administration of dextran sulfate which has been modified with a β2 microglobulin antibody serving as an adsorbent for β2 microglobulin simultaneously with LDL serving as a hepatocyte-specific ligand, can promote active incorporation of β2 microglobulin into hepatocytes.

The present inventors have also found that an LDL-dextran sulfate-protein A complex, which is formed during administration of dextran sulfate to which protein A specifically recognizing an antibody has been incorporated simultaneously with LDL serving as a hepatocyte-specific ligand, can promote active incorporation of a pathogenic antibody occurring in an excessive amount in vivo into hepatocytes.

Therefore, the inventors have found that a compound which is formed by bonding an adsorbent for a pathogen occurring in the blood or lymph to a ligand which is specific to an organ or cells capable of metabolizing or excreting the pathogen, via a linker or with no linker can be employed as an agent for lowering the level of the pathogen occurring in the blood or lymph, whereby a disease caused by the pathogen can be treated. The present invention has been accomplished on the basis of these findings.

Accordingly, the present invention provides a compound which is formed of (A) an adsorbent for a pathogen occurring in the blood or lymph, and (B) a ligand which is specific to an organ or cells capable of metabolizing or excreting the pathogen and which is bonded to the adsorbent via a linker or with no linker.

The present invention also provides an agent for lowering the intracorporeal level of a pathogen occurring in the blood or lymph, which agent contains the compound as an active ingredient.

The present invention also provides a prophylactic and/or therapeutic agent for a disease caused by a pathogen occurring in the blood or lymph, which agent contains the compound as an active ingredient.

The present invention also provides a pharmaceutical composition for preventing and/or treating a disease caused by a pathogen occurring in the blood or lymph, which composition contains the compound and a pharmaceutically acceptable carrier.

The present invention also provides use of the compound for producing a prophylactic and/or therapeutic agent for a disease caused by a pathogen occurring in the blood or lymph.

The present invention also provides use of the compound for producing an agent for lowering the level of a pathogen occurring in the blood or lymph.

The present invention also provides a method for lowering the intracorporeal level of a pathogen occurring in the blood or lymph, including administering an effective amount of the compound to a subject in need thereof.

The present invention also provides a method for preventing and/or treating a disease caused by a pathogen occurring in the blood or lymph, including administering an effective amount of the compound to a subject in need thereof.

Effects of the Invention

According to the present invention, the level of a pathogen occurring in an excessive amount in the blood or lymph can be lowered through administration of a drug to the body without performing hemodialysis or various apheresis techniques. More specifically, a compound falling within the scope of the present invention in which dextran sulfate is modified with galactose has an excellent LDL lowering action, and thus can be employed as a new agent for treating hyperlipidemia. Particularly, the blood LDL level of a patient of severe hyperlipidemia such as homo-type familial hyperlipidemia, which would otherwise require removal of blood LDL through LDL apheresis, can be effectively lowered.

Meanwhile, an LDL-dextran sulfate-$\beta 2$ microglobulin antibody complex, which is formed during administration of dextran sulfate-$\beta 2$ microglobulin antibody simultaneously with LDL has an excellent $\beta 2$ microglobulin lowering action, and thus can be employed as a new agent for treating amyloidosis. Particularly, the blood $\beta 2$ microglobulin level of a patient of severe dialysis amyloidosis, which would otherwise require removal of blood $\beta 2$ microglobulin through high-performance (capable of removing $\beta 2$ microglobulin) artificial kidney or hexadecyl-group-immobilized cellulose beads, can be effectively lowered.

Furthermore, an LDL-dextran sulfate-protein A complex, which is formed during simultaneous administration of LDL and dextran sulfate-protein A, has an excellent action of lowering the level of an antibody which is present in an excessive amount in the body and which causes a disease, and thus can be employed as a new therapeutic agent; e.g., a therapeutic agent for idiopathic dilated cardiomyopathy. Particularly, the blood antibody level of a patient who has been treated through surgical therapy such as heart transplantation due to the absence of effective medical therapy can be lowered.

BEST MODES FOR CARRYING OUT THE INVENTION

The term "pathogen occurring in the blood or lymph" refers to a substance which occurs in an excessive amount in the blood or lymph due to metabolic disorders, excretion failure, difficulty in removal, abnormal proliferation, etc. and which adversely affects body functions. Specific examples thereof include LDL and oxidized LDL in hyperlipidemia patients, $\beta 2$ microglobulin in amyloidosis patients, anti-miocardial self-antibody in dilated cardiomyopathy patients, galactose in galactosuria patients, glycogen and lactic acid in diabetes patients, lactose in lactose intolerance patients, sucrose and fructose in fructose intolerance patients, phenylalanine in phenylketonuria patients, $\alpha$-keto acid in maple-syrupuria patients, histidine in histidinurea patients, propionic acid in propionic-aciduria patients, methyl malonate in methyl-malonaturia patients, porphyrin in porphyria patients, self-antibodies in patients of an autoimmune disease such as systemic lupus erythematosus, scleroderma, multiple myositis, or rhumatoid arthritis, hemosiderin in hemosiderosis patients, copper in Wilson's disease patients, potassium in hyperpotassemia patients, calcium in hpyercalcemia patients, magnesium in hypermagnesemia patients, and fat-soluble vitamin in hyper-fat-soluble-vitaminosis patients.

The term "adsorbent for the pathogen" refers to a substance capable of adsorbing the pathogen in the blood or lymph. Examples of the adsorbent for LDL include anionic polypeptides such as aspartic acid and glutamic acid; high-molecule or low-molecule compounds having an anionic group such as polysaccharide (e.g., dextran sulfate); and polymers having an anionic group such as a carboxyl group. Among them, dextran sulfate or a salt thereof are preferred. Examples of dextran sulfate include those having a molecular weight of 3,000 to 200,000. Among them, those having a molecular weight of 3,000 to 50,000 are preferred, with those having a molecular weight of 36,000 to 50,000 being more preferred. One molecule of dextran sulfate preferably has a sulfur atom content of 3 to 10 wt. %. Examples of the salt of dextran sulfate include alkali metal (e.g., sodium or potassium) salts thereof. Among them, sodium salts are preferred. Examples of the adsorbent for $\beta 2$ microglobulin include peptides and antibodies specifically recognizing $\beta 2$ microglobulin and compounds specifically adsorbing $\beta 2$ microglobulin such as calcium hydroxide phosphate. Examples of the adsorbent for an antibody include protein A, which is bound specifically to the antibody.

Examples of the organ or cells capable of metabolizing or excreting the pathogen include the liver, hepatocytes, the kidney, kidney cells, the spleen, the lung, and the malpighian tube. Among them, the liver, hepatocytes, the kidney, kidney cells, etc. are preferred, with the liver and hepatocytes being more preferred.

Examples of the ligand specific to the organ or cells include ligands which bond to a receptor present in the organ or cells. Particularly, a ligand which bonds to a receptor present in the organ or cells and which can be incorporated into the organ or cells is preferred. This is because, when the ligand per se is capable of being incorporated into the organ or cells to which the ligand has been bonded, the pathogen bonded to the ligand is also incorporated thereinto.

Among such ligands, examples of the ligand specific to hepatocytes include asialoorosomucoid receptor ligands (e.g., galactose, lactose, monogalactosyl diacylglycerol, agarose, and carrageenan), LDL, Fas, albumin, ApoE, and ApoB. Among them, galactose (asialoorosomucoid receptor ligand) and LDL are preferred.

The aforementioned adsorbent may be bonded to the ligand by the mediation of a linker or may be directly bonded.

Examples of the linker include diamines and glycols such as propylenediamine, trimethylenediamine, hexamethylenediamine, and polyethylene glycol, each member having a carbonyl group at each end. Specific examples include —CONH—$(CH_2)_l$—NHCO— and —CO—$(OCH_2CH_2)_m$—OCO— (wherein each of l and m is a number of 1 to 100).

No particular limitation is imposed on the linkage structure of between the adsorbent and ligand (including a case where a linker is employed). Examples of the linkage formation include formation of covalent bonds such as amido bond, urethane bond, urea bond, ester bond, disulfide bond, and ether bond; adsorption via antibody-antigen reaction; and formation of non-covalent bonds such as formation of ionic bond and hydrophobic interaction. In the case where dextran sulfate is bonded to galactose, preferably, the ligand and the adsorbent are linked to each other through formation of urethane bonds by the mediation of a linker.

The following is an example of reactions for the introduction of galactose to dextran sulfate.

No particular limitation is imposed on the activating agent, so long as it is a reagent which can be used for activating a hydroxyl group. Examples of the agent include carbonyldiimidazole (CDI) and N,N'-disuccinimidylcarbonate (DSC). Through use of the agents, an imidazolecarbamate group and a succinimidylcarbamate group are incorporated into dextran sulfate. Examples of the reaction solvent which may be used include formamide and DMSO. The reaction may be performed at 0 to 40° C. (preferably 25 to 37° C.). The reaction time is preferably 0.5 to 12 hours, particularly preferably 1 to 3 hours.

In step 2, dextran sulfate having a carbonyl group produced in step 1 is reacted with alkylenediamine to thereby form an amido group.

A linear C1 to C100 alkylenediamine may be used, and a C3 to C50 alkylenediamine is preferably used. Examples of the reaction solvent which may be used include formamide (wherein R represents a sulfonate residue or a hydrogen atom; A represents a leaving group; and n is an integer of 1 to 100)

In step 1, dextran sulfate is reacted with an activating agent to thereby incorporate an intermediate which reacts with an amino group into some positions of dextran sulfate.

and DMSO. The reaction may be performed at 0 to 40° C. (preferably 25 to 37° C.). The reaction time is preferably 0.5 to 24 hours, particularly preferably 5 to 16 hours.

Step 1 and step 2 may be performed simultaneously in one pot.

In step 1, galactose is reacted with an activating agent to thereby incorporate an intermediate which reacts with an amino group into galactose.

The same activating agents as mentioned above may also be used. Examples of the reaction solvent which may be used include formamide and DMSO. The reaction may be performed at 0 to 40° C. (preferably 25 to 37° C.). The reaction time is preferably 0.5 to 12 hours, more preferably 1 to 3 hours.

In step 3, the amino group of the compound produced in step 2 is reacted with the compound produced in step i to thereby form an urethane bond, whereby a compound in which galactose is incorporated to the target dextran sulfate is obtained.

Examples of the reaction solvent which may be used include formamide and DMSO. The reaction may be performed at 0 to 40° C. (preferably 25 to 37° C.). The reaction time is preferably 0.5 to 24 hours, more preferably 15 to 21 hours.

In a preferred mode, galactose (150 to 200 mol) is reacted with dextran sulfate (1 mol). A dextran sulfate (1 mol) modified with galactose (1 to 20 mol) is preferred.

In step 4, an antibody is reacted with a cleaving reagent to thereby cleave the Fc fragment from the antibody. No particular limitation is imposed on the cleaving reagent, so long as the reagent is a chemical product, an enzyme, or the like which can completely or partially cleave the Fc fragment from the antibody. Particularly, pepsin is preferred. No particular limitation is imposed on the reaction solvent, so long as the solvent does not impede reaction and can maintain activity of the antibody. Examples of the solvent which may be used include phosphate buffer and Tris buffer. The reaction may be performed at 0 to 100° C. (preferably 25 to 40° C.). The reaction time is preferably 0.5 to 48 hours, more preferably 24 to 48 hours.

In step 5, the F(ab')$_2$ antibody produced in step 4 is reacted with a reducing agent to thereby cleave a disulfide bond.

As used herein, the term "reducing agent" refers to a reagent which is capable of cleaving a disulfide bond of an antibody. Particularly, 2-mercaptoetylamine, dithiothreitol, etc, are preferably used. The reaction may be performed for 30 minutes to 12 hours (preferably 60 minutes to 90 minutes). The reaction temperature is preferably 4 to 40° C., more preferably 30 to 40° C.

In step 6, the amino-group-incorporated dextran sulfate produced in step 2 is reacted with an activating agent to thereby form an intermediate which can react with the antibody produced in step 5.

No particular limitation is imposed on the activating agent, so long as the agent can be used for activating an amino group. Examples of the agent include sulfosuccinimidyl-4-(N-maleimidomethyl)cyclohexane-1-carboxylate (sulfo-SMCC) and N-succinimidyl(4-iodoacetyl)aminobenzoate. Examples of the reaction solvent which may be used include water and DMSO. The reaction may be performed at 0 to 50° C. (preferably 25 to 37° C.). The reaction time is preferably 0.5 to 12 hours, more preferably 1 to 5 hours.

In step 7, the compound produced in step 6 is reacted with the thiol group of the compound produced in step 5 to thereby form a thioether bond, whereby a compound in which the F(ab')$_2$ antibody is incorporated to the target dextran sulfate is obtained.

Examples of the reaction solvent which may be used include DMSO and a buffer. The reaction may be performed at 0 to 50° C. (preferably 25 to 37° C.). The reaction time is preferably 0.5 to 72 hours, particularly preferably 12 to 40 hours. Preferably, F(ab')$_2$ antibody (1 mol) is reacted with dextran sulfate (1,000 to 2,000 mol).

In step 8, the amino-group-incorporated dextran sulfate produced in step 2 is reacted with an activating agent to thereby form an intermediate which can react with protein A.

No particular limitation is imposed on the activating agent, so long as the agent can be used for activating an amino group. Examples of the agent include disuccinimidyl tartrate (DST) and glycobis(succinimidylsuccinate) (EGS). Examples of the reaction solvent which may be used include water and DMSO. The reaction may be performed at 0 to 50° C. (preferably 25 to 37° C.). The reaction time is preferably 0.5 to 12 hours, more preferably 1 to 3 hours.

In step 9, the compound produced in step 8 is reacted with the amino group of protein A to thereby form an amido bond, whereby a compound in which protein A is incorporated to the target dextran sulfate is obtained.

Examples of the reaction solvent which may be used include DMSO and a buffer. The reaction may be performed at 0 to 50° C. (preferably 4 to 37° C.). The reaction time is preferably 0.5 to 72 hours, more preferably 12 to 40 hours. Preferably, protein A (1 mol) is reacted with dextran sulfate (0.5 to 100 mol).

When the compound of the present invention is administered to a subject, a pathogen occurring in the blood or lymph is adsorbed by the aforementioned adsorbent and bound to the aforementioned organ or cells by the mediation of the ligand. Eventually, the pathogen is incorporated into the organ or cells. Thereafter, the pathogen is metabolized in or excreted from the organ or cells, whereby the intracorporal pathogen level of the blood or lymph decreases. Therefore, the compound of the present invention serves as a useful prophylactic and/or therapeutic agent for a disease caused by a pathogen occurring in the blood or lymph.

One preferred embodiment of the present invention is a compound which is formed of an LDL adsorbent, and an asialoorosomucoid receptor ligand bonded to the adsorbent via a linker or with no linker. Particularly preferred is a compound which is formed of dextran sulfate, and galactose bonded to destran sulfate via a linker or with no linker (hereinafter may be referred to as dextran sulfate-galactose modified form). The compound has excellent LDL-lowering action and thus, can serve as a prophylactic and/or therapeutic agent for hyperlipidemia. More specifically, blood LDL is adsorbed by the dextran sulfate moieties of the dextran sulfate-galactose modified form and delivered to the liver. Then, the galactose moieties of the dextran sulfate-galactose modified form act on the asialoorosomucoid receptors which are widely present on the surfaces of hepatocytes, whereby blood LDL is incorporated into hepatocytes. This phenomenon is based on the mechanism (metabolic switching mechanism), in which the drug switches the metabolism route to a new route on which blood LDL conventionally does not act. Eventually, blood LDL is decomposed in the liver. In the switching mechanism, since a plurality of galactose moieties are incorporated to side chains of dextran sulfate-galactose modified form (high molecular weight), bonding of galactose moieties of the modified form side chains with respect to the asialoorosomucoid receptor is promoted more effectively as compared with single galactose molecules. Therefore, the dextran sulfate-galactose modified form, which is a polymer compound, can attain more efficient lowering of blood LDL by the mediation of the liver.

Another preferred embodiment of the present invention is a compound which is formed of a β2 microglobulin adsorbent, and a hepatocyte-specific ligand or a molecule which can be adsorbed by a hepatocyte-specific ligand. Particularly preferred is a complex which is formed of dextran sulfate modified with a β2 microglobulin antibody, and LDL which serves as a hepatocyte-specific ligand. The compound has excellent β2-microglobulin-incorporating action and thus, can serve as a prophylactic and/or therapeutic agent for dialysis amyloidosis. More specifically, LDL which has been separately administered to the body or originally occurs in the body is adsorbed by the dextran sulfate moieties of the dextran sulfate modified with a β2 microglobulin antibody to thereby form the aforementioned complex. The β2 microglobulin antibody moieties adsorb β2 microglobulin, which is then delivered to hepatocytes. Then, the LDL moieties of the complex act on the LDL receptors which are widely present on the surfaces of hepatocytes. According to the metabolic switching mechanism, β2 microglobulin is incorporated into hepatocytes and decomposed in the liver. Alternatively, a β2 microglobulin antibody-dextran sulfate-LDL complex may be prepared in advance, and the prepared complex may be administered to a subject.

Still another preferred embodiment of the present invention is a compound which is formed of an antibody adsorbent, and a hepatocyte-specific ligand or a molecule which can be adsorbed by a hepatocyte-specific ligand. Particularly preferred is a complex which is formed of dextran sulfate modified with protein A, and LDL which serves as a hepatocyte-specific ligand. The compound has excellent antibody-incorporating action and thus, can serve as a prophylactic and/or therapeutic agent for, for example, idiopathic dilated cardiomyopathy. More specifically, LDL which has been separately administered to the body or originally occurs in the body is adsorbed by the dextran sulfate moieties of the dextran sulfate modified with protein A to thereby form the aforementioned complex. The protein A moieties adsorb an antibody, which is then delivered to hepatocytes. Then, the LDL moieties of the complex act on the LDL receptors which are widely present on the surfaces of hepatocytes. According to the metabolic switching mechanism, the antibody is incorporated into hepatocytes and decomposed in the liver. Alternatively, an protein A-dextran sulfate-LDL complex may be prepared in advance, and the prepared complex may be administered to a subject.

As described above, according to the metabolic switching mechanism, the compound of the present invention allows a pathogen accumulated in the blood to alter the metabolizing route in which the pathogen is directly involved to another route, whereby metabolizing or excreting the pathogen can be promoted.

The drug of the present invention contains, an active ingredient, the compound of the present invention. No particular limitation is imposed on the dosage form, and it can be appropriately selected according to therapeutic purposes. Examples of the dosage form include oral solid preparations, oral liquid preparations, injections, suppositories, topical agents, eye drops, nasal drops, ear drops, and adhesive preparations. The drug in any of these dosage forms may be manufactured through a common preparation method known by those skilled in the art by mixing the compound of the present invention with a pharmaceutically acceptable carrier.

When the oral solid preparation is prepared, the compound of the present invention may be supplemented with an excipient and optionally with a binder, a disintegrant, a lubricant, a coloring agent, a flavoring agent, an odor-improving agent, and the like, and then the mixture is processed into tablets, granules, powder, capsules, or the like, by a routine method. Such additives may be those generally used in the art, and examples thereof include lactose, sodium chloride, sucrose, starch, microcrystalline cellulose, and silicic acid as the excipient; water, ethanol, propanol, simple syrup, gelatin solution, hydroxypropylcellulose, methylcellulose, ethylcellulose, shellac, calcium phosphate, and polyvinylpyrrolidone as the binder; agar powder, sodium hydrogencarbonate, sodium lauryl sulfate, and stearic acid monoglyceride as the disintegrant; purified talc, stearate, borax, and polyethylene glycol as the lubricant; β-carotene, yellow iron sesquioxide, and caramel as the coloring agent; and white sugar and orange peels as the flavoring agent.

When the oral liquid preparation is prepared, the compound of the present invention may be supplemented with a flavoring agent, a buffer, a stabilizer, a preservative, and the like to thereby produce an oral liquid medicine, a syrup, an elixir, or the like by a routine method. Such additives may be those generally used in the art, and examples include white sugar as the flavoring agent, sodium citrate as the buffer, traganth as the stabilizer, and p-hydroxybenzoic acid esters as the preservative.

When the injection is prepared, the compound of the present invention may be supplemented with a pH regulator, a stabilizer, a tonicity agent, and the like to thereby produce hypodermic, intramuscular, and intravenous injections by a routine method. Such additives may be those generally used in the art, and examples include sodium phosphate as the pH regulator, sodium pyrosulfite as the stabilizer, and sodium chloride as the tonicity agent.

When the suppository is prepared, the compound of the present invention may be supplemented with a carrier and a surfactant to thereby produce a suppository by a routine method. Such additives may be those generally used in the art, and examples include polyethylene glycol and hard fat as the carrier and polysorbate 80 as the surfactant.

When the topical agent is prepared, the compound of the present invention may be supplemented with a base, a water-soluble polymer, a solvent, a surfactant, a preservative, and the like, to thereby produce a liquid preparation, a cream, a gel preparation, an ointment, or the like, by a routine method. Examples of the additives include liquid paraffin, white Vaseline, and purified lanolin as the base; carboxyvinyl polymers as the water-soluble polymer; glycerin and water as the solvent; polyoxyethylene fatty acid esters as the surfactant; and p-hydroxybenzoic acid esters as the preservative.

When the eye drop is prepared, the compound of the present invention may be supplemented with a pH regulator, a stabilizer, a tonicity agent, a preservative, and the like, to thereby produce an eye drop by a routine method. Such additives may be those generally used in the art, and examples include sodium phosphate as the pH regulator, sodium pyrosulfite and EDTA as the stabilizer, sodium chloride as the tonicity agent, and chlorobutanol as the preservative.

When the nasal drop is prepared, the compound of the present invention may be supplemented with a pH regulator, a stabilizer, a tonicity agent, a preservative, and the like, to thereby produce a nasal drop by a routine method. Such additives may be those generally used in the art, and examples include sodium phosphate as the pH regulator, sodium pyrosulfite and EDTA as the stabilizer, sodium chloride as the tonicity agent, and benzalkonium chloride as the preservative.

When the ear drop is prepared, the compound of the present invention may be supplemented with a pH regulator, a buffer, a stabilizer, a tonicity agent, a preservative, and the like, to thereby produce an ear drop by a routine method. Such additives may be those generally used in the art, and examples include sodium phosphate as the pH regulator and the buffer, sodium pyrosulfite and EDTA as the stabilizer, sodium chloride as the tonicity agent, and benzalkonium chloride as the preservative.

When the adhesive preparation is prepared, the compound of the present invention may be supplemented with an adhesive, a solvent, a cross-linking agent, a surfactant, and the like, to thereby produce a hydrous adhesive preparation, an adhesive plaster, or the like, by a routine method. Such additives may be those generally used in the art, and examples include partially neutralized polyacrylic acid, sodium polyacrylate, 2-ethylhexyl polyacrylate, and styrene-isoprene-styrene block copolymers as the adhesive; glycerin and water as the solvent; dihydroxy aluminum aminoacetate and dried aluminum hydroxide gel as the cross-linking agent; and polyoxyethylene fatty acid ester as the surfactant.

The dose of the drug of the present invention varies depending on, for example, age, body weight, condition, dosage form, and the number of doses. In general, it is preferred that the drug be administered orally or parenterally to an adult at single dose or doses divided into several times, of 1 to 1,000 mg per day in terms of the amount of the compound of the present invention.

EXAMPLES

The present invention will next be described in detail by way of examples, which should not be construed as limiting the invention thereto.

Example 1

Synthesis of Dextran Sulfate-Galactose Complex

To formamide (25 mL) serving as a solvent, soluble dextran sulfate having a molecular weight of 36,000 to 50,000 (125 mg, 2.5 to 3.4 mmol), 1,6-hexamethylenediamine (67.4 mg, 581 μmol) serving as a linker molecule, and 1,1'-carbonyldiimidazole (78 mg, 484 μmol) serving as an activating agent were added. The mixture was allowed to react at 37° C. for 19 hours to thereby incorporate 1,6-hexamethylenediamine (linker) to side-chain hydroxyl groups of dextran sulfate.

Subsequently, D-(+)-galactose (34.7 mg, 193 mmol) was added to formamide (10 mL), and 1,1'-carbonyldiimidazole (37.5 mg, 232 mmol) serving as an activating agent was further added thereto. The mixture was allowed to react at 37° C. for 2 hours. Thereafter, hexamethylenediamine-incorporated dextran sulfate (56 mg, 1.1 to 1.5 μmol) was added to the reaction, and the resultant mixture was allowed to react at 37° C. for 21 hours. Through routine purification and separation, 33 mg (0.6 to 0.9 μmol) of the title compound was yielded (yield: 55%).

$^1$H-NMR: $^1$H (dextran sulfate, galactose) δ: 3.2-5.2 ppm, $^1$H (linker CH$_2$) δ: 1.2-1.6 ppm.

Example 2

Blood LDL-Lowering Action

Figure 1:
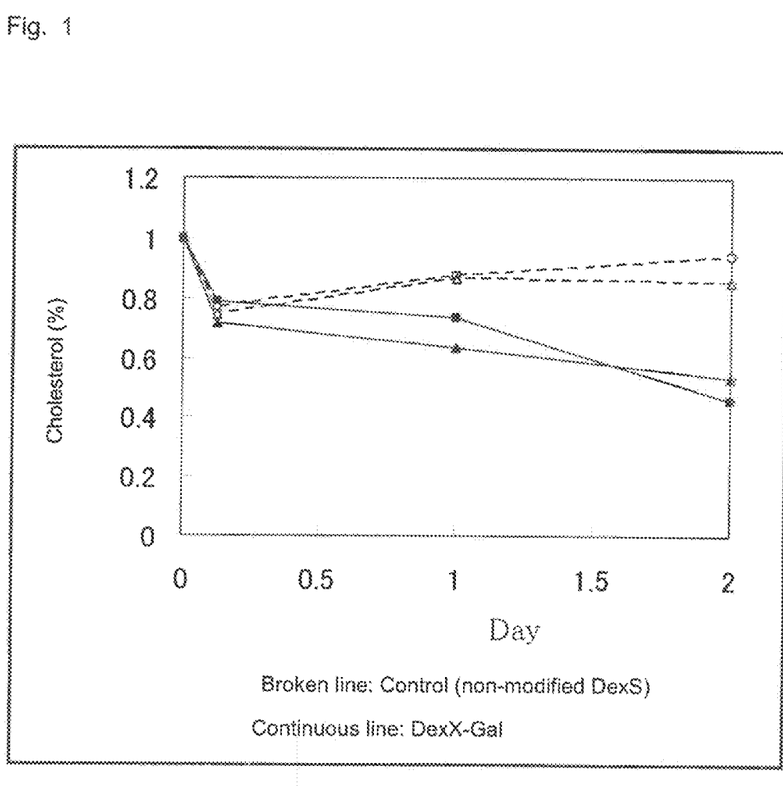
FIG. 1 is a graph showing changes in cholesterol level of hyperlipidemia-model mice after injection of dextran sulfate-galactose.

Toxicity and efficacy of the drug produced in Example 1 were investigated. To LDL-receptor•apoE double knocked-out mice (n=2), 2 g/L dextran sulfate-galactose solution (0.1 mL) and 2 g/L dextran sulfate solution (control) (0.1 mL) were administered once through the carotid artery. The blood cholesterol level was monitored through the cholesterol oxidase DAOS method. FIG. 1 shows the results.

As is clear from FIG. 1, only in the dextran sulfate-galactose modified form administration group, more effective lowering of blood cholesterol level was observed for two days, as compared with the control (non-modified dextran sulfate administration group).

Example 3

Synthesis of Dextran Sulfate-β2 Microglobulin Antibody

Pepsin-immobilized resin was washed with 20 mM acetate buffer (pH: 4.5), and the washed resin was suspended in acetate buffer (pH: 4.5) (1 mL). β2 microglobulin antibody (50 μg) was added to the suspension and incubated at 37° C. for 24 hours. After incubation, the incubate was centrifuged at 15,000 rpm for three minutes. A portion (1 mL) of the supernatant was recovered and neutralized with 100 mM Tris-HCl buffer (pH: 8.0) (30 μL). The resultant liquid was purified through a protein A-immobilized column to remove unreacted products, whereby an F(ab')$_2$ antibody was isolated. Subsequently, 2-mercaptoethylamine (12 mg) was added to the thus-produced F(ab')$_2$ antibody (190 μg), followed by diluting with PBS to the volume of 1 mL. The antibody was incubated at 37° C. for two hours, and the incubate was purified through Sephadex G-25 column. The purified product was concentrated by means of an ultrafiltration membrane (3 kDa cut), to thereby yield 500 μL of F(ab')$_2$ reduced-form antibody solution.

Figure 2:
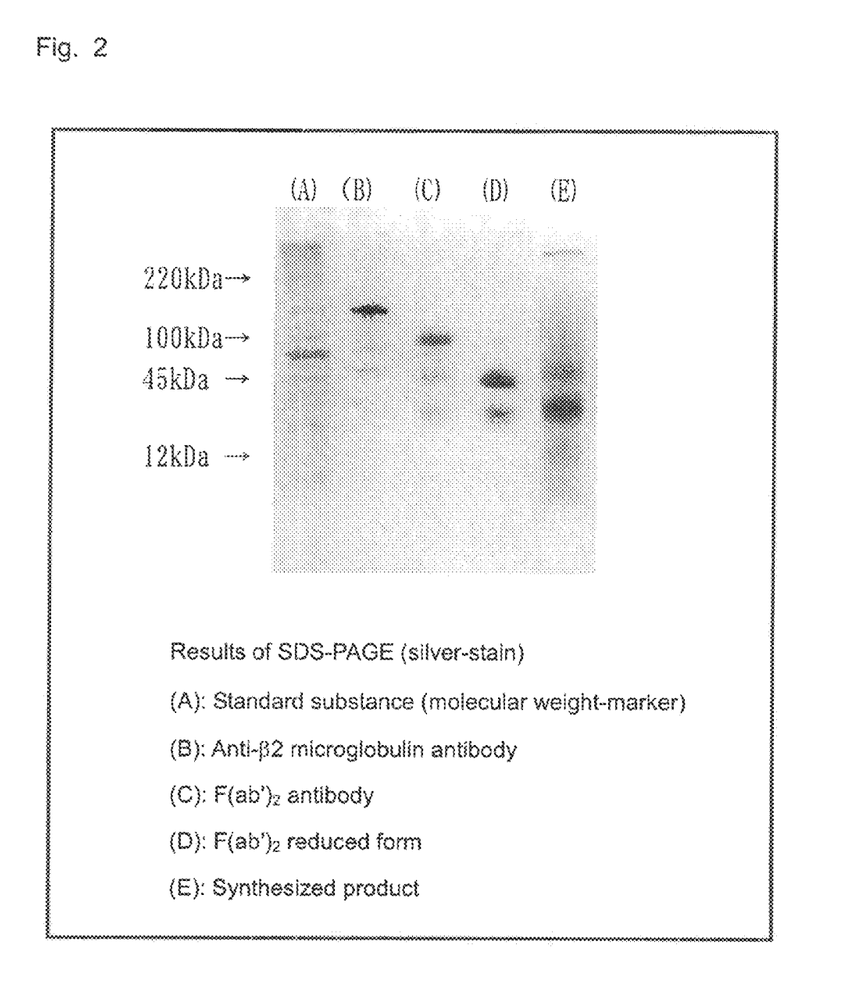
FIG. 2 shows the results of SDS-PAGE of synthesized dextran sulfate-$\beta 2$ microglobulin antibody.

To hexamethylenediamine-incorporated dextran sulfate (72 mg, 1.0 to 1.3 μmol) produced through employment of same procedure and conditions as employed in Example 1, sulfo-SMCC (100 mg, 229 μmol) was added. The mixture was allowed to react in phosphate buffer (15 mL) at 37° C. for 5 hours. The reaction was concentrated by means of an ultrafiltration membrane (3 kDa cut), to thereby yield 500 μL of amino-group-activated dextran sulfate. Thereafter, the thus-yielded dextran sulfate solution was mixed with the F(ab')$_2$ reduced-form antibody solution (500 μL), and the mixture was allowed to react at 37° C. for 40 hours. Further, an equiamount of 5 mM cysteine solution was added to the reaction mixture, and the resultant mixture was allowed to react at 37° C. for 5 hours. The reaction product was concentrated by means of an ultrafiltration membrane, to thereby yield 79 μg (calculated by determination of protein through the BCA method) of the title compound. FIG. 2 shows the results of SDS-PAGE of synthesized dextran sulfate-β2 microglobulin antibody.

Example 4

Blood β2 Microglobulin Level-Lowering Action

Figure 3:
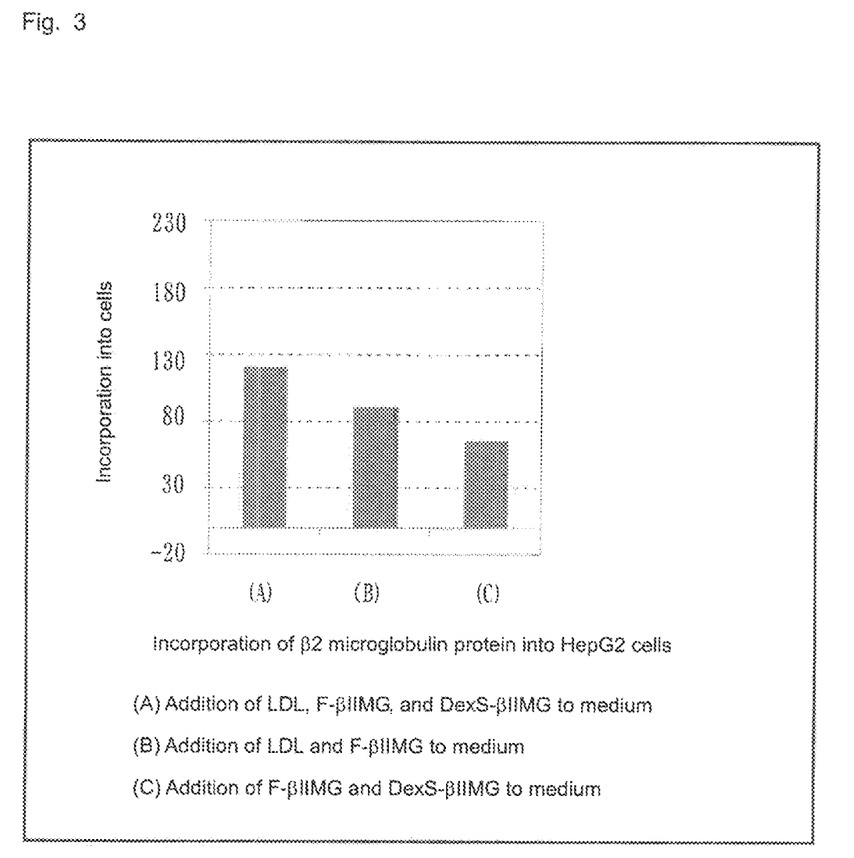
FIG. 3 is a graph showing incorporation of $\beta 2$ microglobulin into HepG2 cells by LDL and dextran sulfate-$\beta 2$ microglobulin antibody.

HepG2 cells (human hepatocytes) were inoculated to a 96-well plate at 4.5×10$^3$ cells/well, followed by incubation for 24 hours. Separately, low-density lipoprotein (LDL) (0.1 μg, 1.8 μmol), fluorescein-modified β2 microglobulin (F-βI-IMG) (31 μg, 2.6 nmol), and the above synthesized dextran sulfate-β2 microglobulin antibody (DexS-βIIMG) (2.3 μg, 26 nmol) were added to a medium (1 mL), and the mixture was further added to the 96-well plate, followed by incubation at 37° C. for 3 hours. The recovered cells were washed with phosphate buffer (100 μL) and lysed. The fluorescent intensity of the thus-obtained solution was measured. FIG. 3 shows the results.

As shown in FIG. 3, as compared with a control medium to which no LDL had been added and another control medium to which no dextran sulfate-β2 microglobulin antibody had been added, a medium to which both LDL and dextran sulfate-β2 microglobulin antibody had been added exhibited incorporation of a larger amount of β2 microglobulin into hepatocytes. That is, β2 microglobulin was found to be incorporated specifically into HepG2 cells by the mediation of an LDL-dextran sulfate-β2 microglobulin antibody complex.

Example 5

Synthesis of Dextran Sulfate-Protein A

Figure 4:
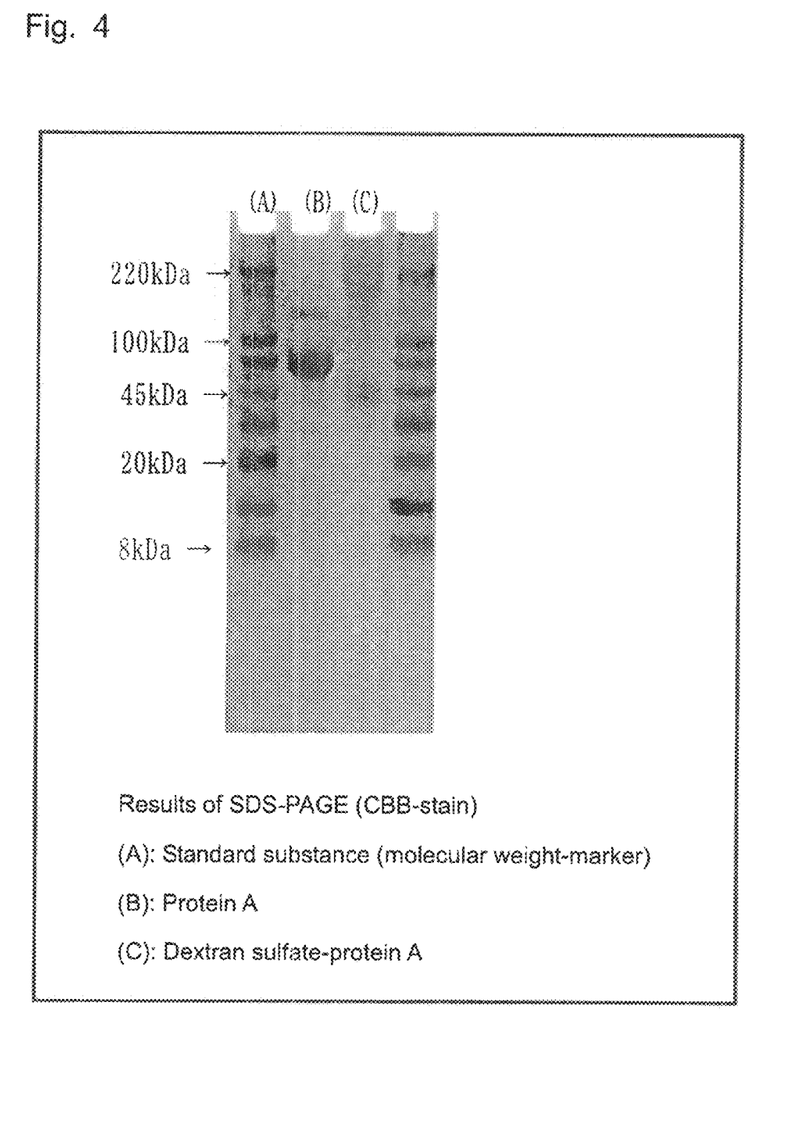
FIG. 4 shows the results of SDS-PAGE of synthesized dextran sulfate-protein A.

To hexamethylenediamine-incorporated dextran sulfate (1.4 mg, 23 nmol, percent ammination: 61.3%/unit) produced through employment of same procedure and conditions as employed in Example 1, DST (4.4 mg, 12.88 μmol) was added. The mixture was allowed to react in 0.2M sodium carbonate buffer (pH: 9.4) (200 μL) at room temperature for one hour. The reaction was purified and concentrated by means of an ultrafiltration membrane (30 kDa), to thereby yield 250 μL of amino-group-activated dextran sulfate. Further, the thus-obtained dextran sulfate was mixed with protein A (100 μL, 1 mg, 23 nmol), and the resultant mixture was allowed to react at 37° C. for 40 hours. The reaction product was purified and concentrated by means of an ultrafiltration membrane (50 kDa), to thereby yield 169 μg (calculated by determination of protein through the BCA method) of the title compound. FIG. 4 shows the results of SDS-PAGE of synthesized dextran sulfate-protein A.

Example 6

Blood Antibody Level-Lowering Action

Figure 5:
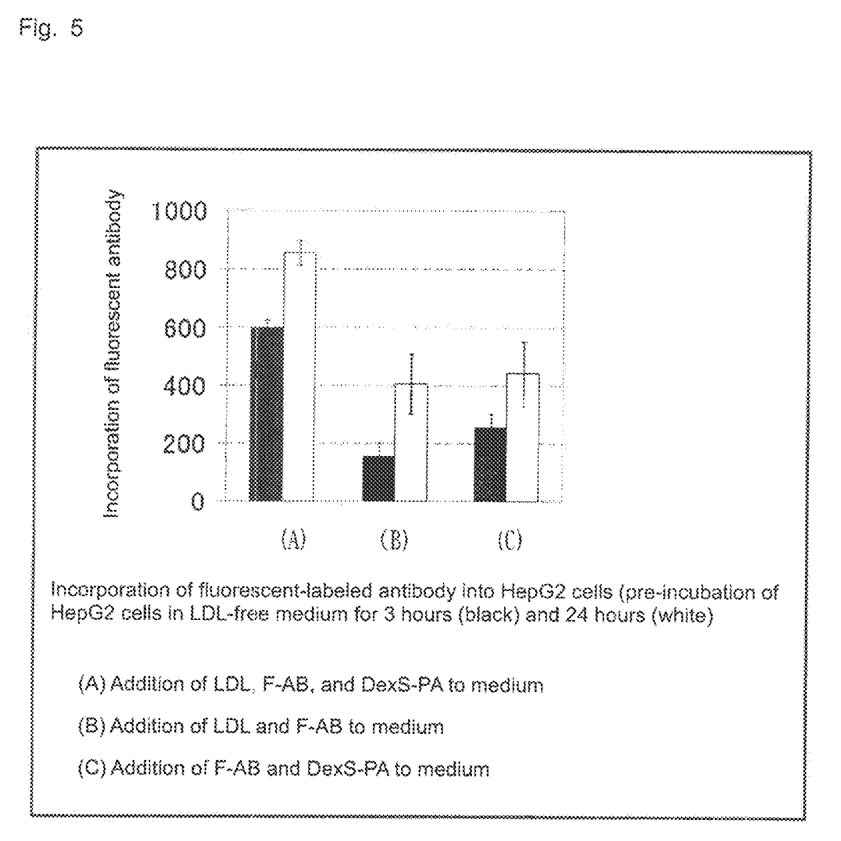
FIG. 5 is a graph showing incorporation of an antibody by LDL and dextran sulfate-protein A.

HepG2 cells (human hepatocytes) were inoculated to a 96-well plate at $4.5 \times 10^3$ cells/well, followed by incubation for 24 hours. Thereafter, a medium (100 μL) containing 10% of low-density lipoprotein-free serum (LDL-free medium) was further added thereto, followed by incubation for 3 or 24 hours. Separately, low-density lipoprotein (LDL) (0.1 μg, 1.8 μmol), fluorescein-modified rabbit anti-mouse IgG antibody (27.3 μg, 182 μmol), and the above-synthesized dextran sulfate-protein A (2.04 μg, 18.2 pmol) were added to LDL-free medium (1 mL), and the mixture (100 μL) was further added to the 96-well plate, followed by incubation at 37° C. for 3 hours. The recovered cells were washed with phosphate buffer (100 μL) and lysed. The fluorescent intensity of the thus-obtained solution was measured. FIG. 5 shows the results.

As shown in FIG. 5, as compared with a control medium to which no dextran sulfate-protein A had been added and another control medium to which no LDL had been added, a medium to which both LDL and the synthesized dextran sulfate-protein A had been added exhibited a significant increase in incorporation of fluorescent-modified antibody into hepatocytes. That is, the synthesized dextran sulfate-protein A was found to be capable of incorporating the antibody specifically into HepG2 cells through formation of the LDL-dextran sulfate-protein A complex.

The invention claimed is:

1. A compound which is formed of (A) an adsorbent for a pathogen occurring in the blood or lymph, and (B) a ligand which is specific to hepatocytes and which is bonded to the adsorbent via a linker having carbonyl group at each end of diamine or glycol, wherein the adsorbent (A) is dextran sulfate or a salt thereof, or dextran sulfate or a salt thereof which is modified with the adsorbent (A).

2. The compound according to claim 1, wherein the pathogen occurring in the blood or lymph is LDL, and the ligand is an asialoorosomucoid receptor ligand.

3. The compound according to claim 2, wherein the ligand is galactose.

4. The compound according to claim 2 or 3, wherein the adsorbent for LDL is dextran sulfate or a salt thereof.

5. The compound according to claim 1, wherein the pathogen occurring in the blood or lymph is β2 microglobulin, and the ligand is LDL.

6. The compound according to claim 5, wherein the adsorbent for β2 microglobulin is dextran sulfate which has been modified with a β2 microglobulin antibody or a salt thereof.

7. The compound according to claim 1, wherein the pathogen occurring in the blood or lymph is an antibody, and the ligand is LDL.

8. The compound according to claim 7, wherein the adsorbent for the antibody is dextran sulfate which has been modified with protein A or a salt thereof.

* * * * *